Figure 1:
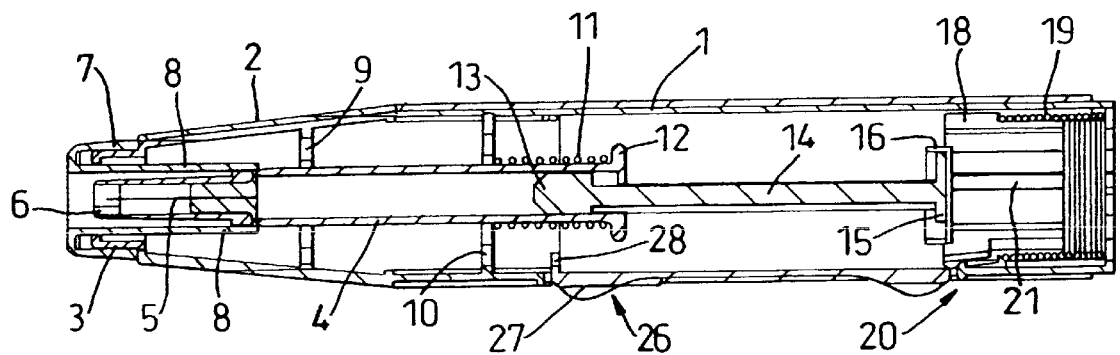

United States Patent [19]
Crossman et al.

[11] Patent Number: 6,159,181
[45] Date of Patent: Dec. 12, 2000

[54] INJECTION DEVICE

[75] Inventors: David Danvers Crossman; Jeremy Marshall, both of Oxford; Glenn Davison, Banbury, all of United Kingdom

[73] Assignee: Owen Mumford Limited of Brook Hill, Oxford, United Kingdom

[21] Appl. No.: 09/446,186

[22] PCT Filed: Apr. 16, 1999

[86] PCT No.: PCT/GB99/01184

§ 371 Date: Dec. 17, 1999

§ 102(e) Date: Dec. 17, 1999

[87] PCT Pub. No.: WO99/53979

PCT Pub. Date: Oct. 28, 1999

[51] Int. Cl.[7] .................................................. A61M 5/20
[52] U.S. Cl. ........................... 604/157; 604/134; 604/135
[58] Field of Search ................................. 604/157, 134, 604/135, 136, 195, 110, 144, 232, 187

[56] References Cited

U.S. PATENT DOCUMENTS 3,880,163  4/1975  Ritterskamp .
5,478,316  12/1995  Bitdinger et al. ....................... 604/135
5,637,094  6/1997  Stewart, Jr. .
5,713,866  2/1998  Wilmot ................................. 604/157 X
5,851,197  12/1998  Marano et al. ...................... 604/157 X

FOREIGN PATENT DOCUMENTS 2 342 079    9/1997   France .
WO 94/21316  9/1994   WIPO .

*Primary Examiner*—John D. Yasko
*Attorney, Agent, or Firm*—Young & Thompson

[57] ABSTRACT

An injection device has a drive spring which, when released, urges a loaded capsule forwards to project its needle from the end of a barrel and ejects the dose. A light return spring then retracts the needle. The drive spring acts on the capsule plunger through a drive member having a movable barrier against which the rear end of the plunger initially abuts. A first trigger releases the drive member and drive spring and after an injection a second trigger can be actuated to shift the barrier relative to the drive member and allow the return spring to act.

10 Claims, 7 Drawing Sheets

INJECTION DEVICE

This invention relates to injection devices, and in articular to one-shot devices which are supplied primed and with a full capsule, and which are thrown away after a single use.

It is important that after the injection has been made, the needle should be made safe, and this is usually done by retraction inside the barrel-like body of the device. This can happen automatically, with a returning spring coming into play when the injection has been made and a connection between the drive mechanism and the capsule has been broken. But it is difficult to ensure that the disconnection of the drive mechanism happens at the right time. In particular, if it happens a bit too early, the return spring will act before the full dose has been ejected. If it is does not happen too early or at just the right moment it probably will not happen at all, because once the full drive stroke has been completed, everything is stationary, and without any movement, no disconnection can be made.

Without automatic retraction, the user has to cause it, and do so in a simple and convenient manner. It is the aim of this invention to provide such a device.

According to the present invention there is provided a one-shot injection device with a barrel-like body carrying a loaded capsule having a needle at its forward end and a spring drive system which, when released, drives the capsule forwards to project the needle from the body and eject a dose through the needle, and which thereafter can cause the capsule and needle to be retracted, wherein the spring drive system comprises a drive spring, a hollow drive member acted upon by the drive spring and initially held in a rearward position by a first trigger, an abutment member between the drive member and the rear end of the plunger whose forward end forms or acts upon a piston within the capsule, a return spring acting between the capsule and the body, and a second trigger operable when the drive member is in a forward position to move the abutment member from an engaged position in relation to the drive member to a disengaged position where the return spring can act to push the abutment member rearwardly via the capsule and its plunger, thereby retracting the needle.

There are preferably removable means to shield the first trigger or to prevent it being accidentally operated when the device is primed.

The drive spring is conveniently a coil spring which when released shoots the drive member and capsule forwards, using the plunger, to project the needle and then eject the dose through the needle, the liquid contents of the capsule acting as a solid while the needle is penetrating.

The drive member can be a cylinder open at both ends and with a rearwardly facing shoulder against which the drive spring acts, the other end of the drive spring reacting against the closed rear end of the barrel.

The return spring is also conveniently a coil spring surrounding the capsule and offering little resistance to the drive spring.

In one form the abutment member is free of the drive member and in its engaged position is peripherally held against a forward facing shoulder formation of the drive member. The second trigger actuation shifts the abutment member to the disengaged position, clear of the shoulder, where it is free to be pushed rearwardly through the drive member. This shift from the engaged to the disengaged position may laterally of the barrel or rotational about the axis of the barrel.

In another preferred form the abutment member is hinged to the drive member and in its engaged position is held across a passage through the drive member by a formation diametrically opposite the hinge co-operating with a detent on the barrel. The shift from the engaged to the dishing gaged position is by the second trigger releasing said formation from the detent, thereby allowing the abutment member to hinge back and clear the passage for the plunger.

Preferably the drive member and the abutment member are integrally moulded of plastics material. A thin web then forms the hinge and will allow diametral shift of the abutment member for the release of said formation from the detent.

Figure 7:
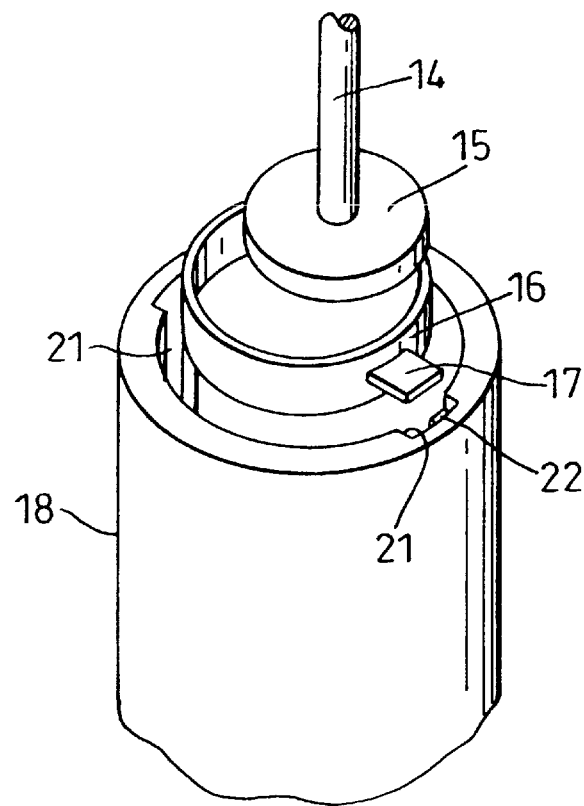
Figure 8:
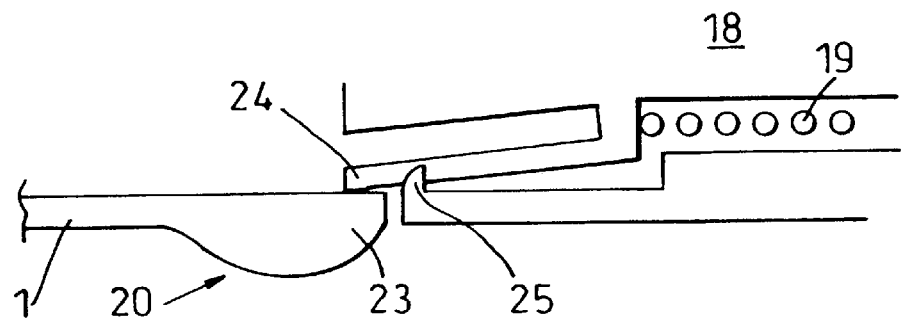
Figure 9A:
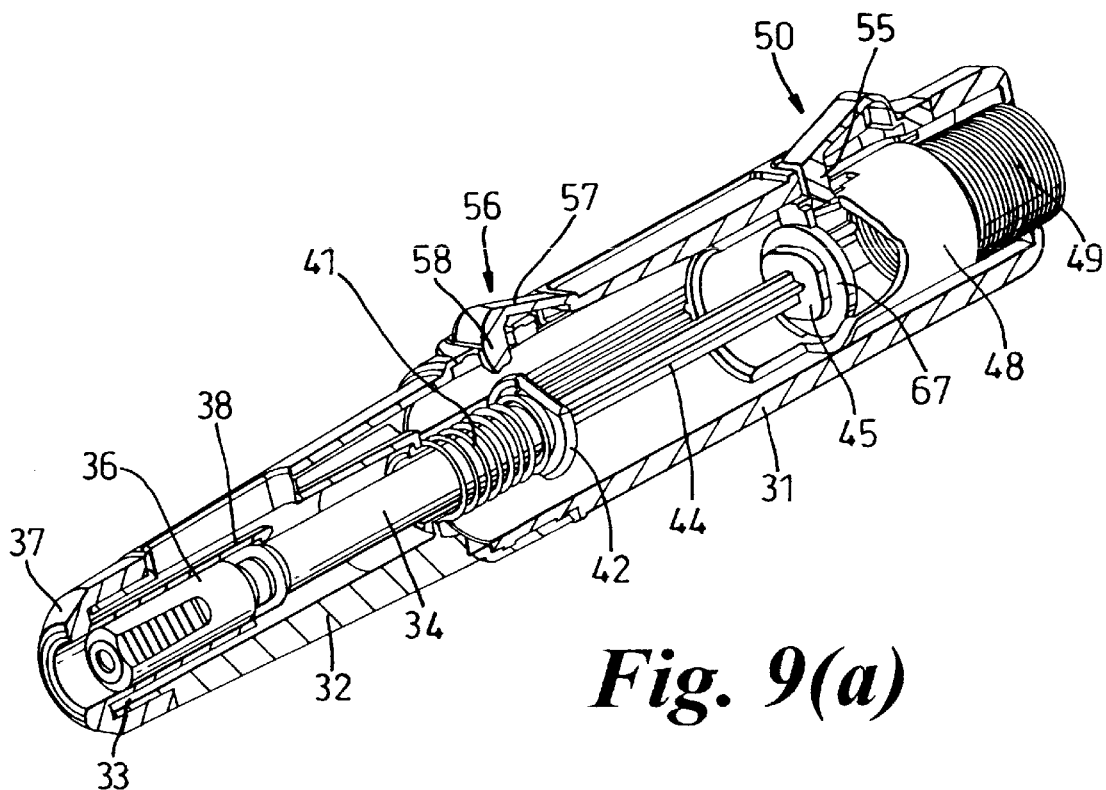
Figure 9B:
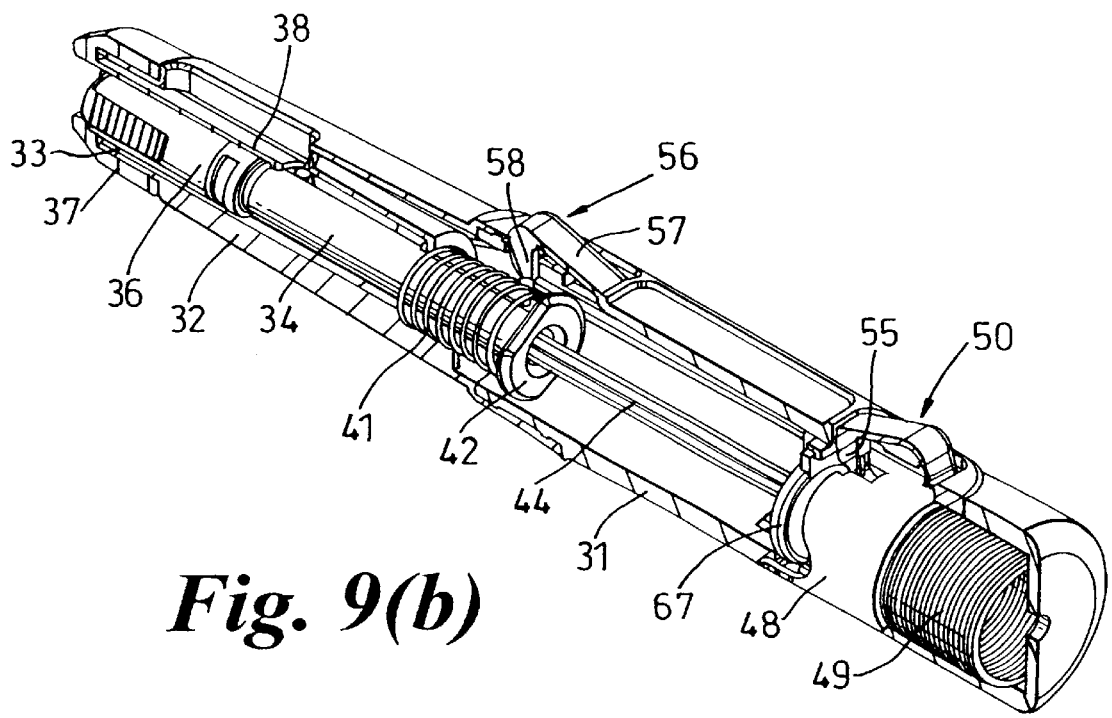
Figure 10A:
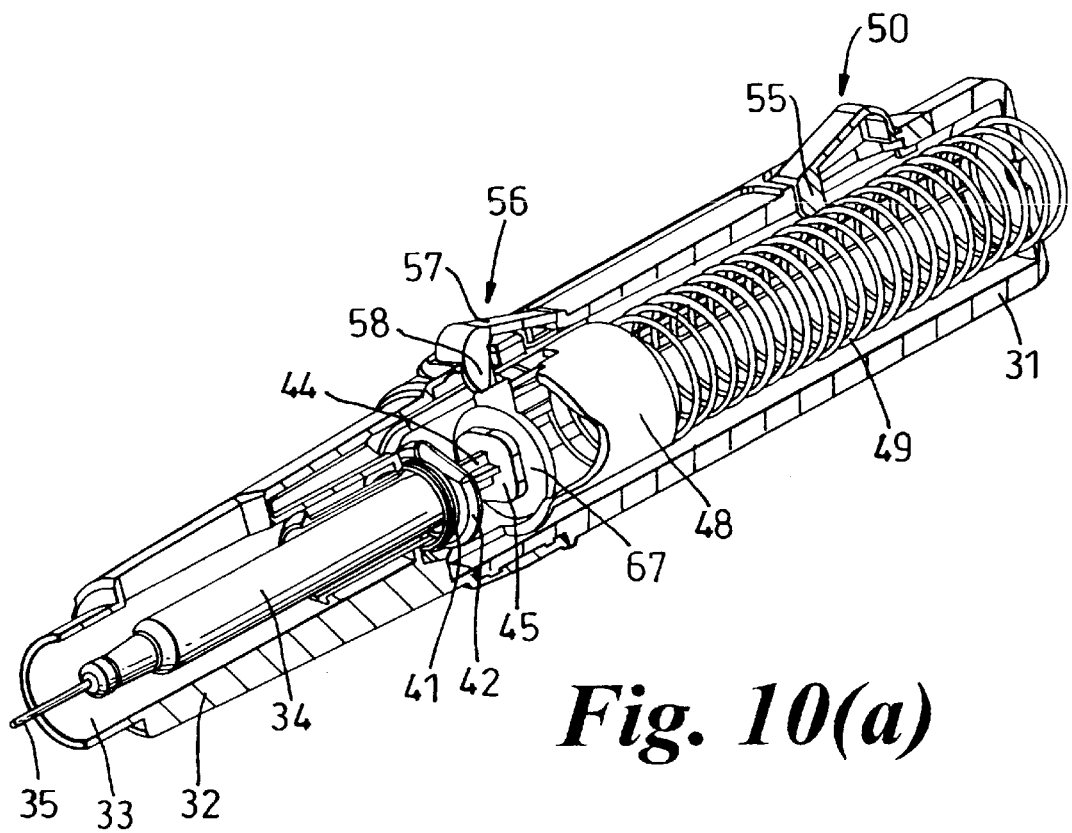
Figure 10B:
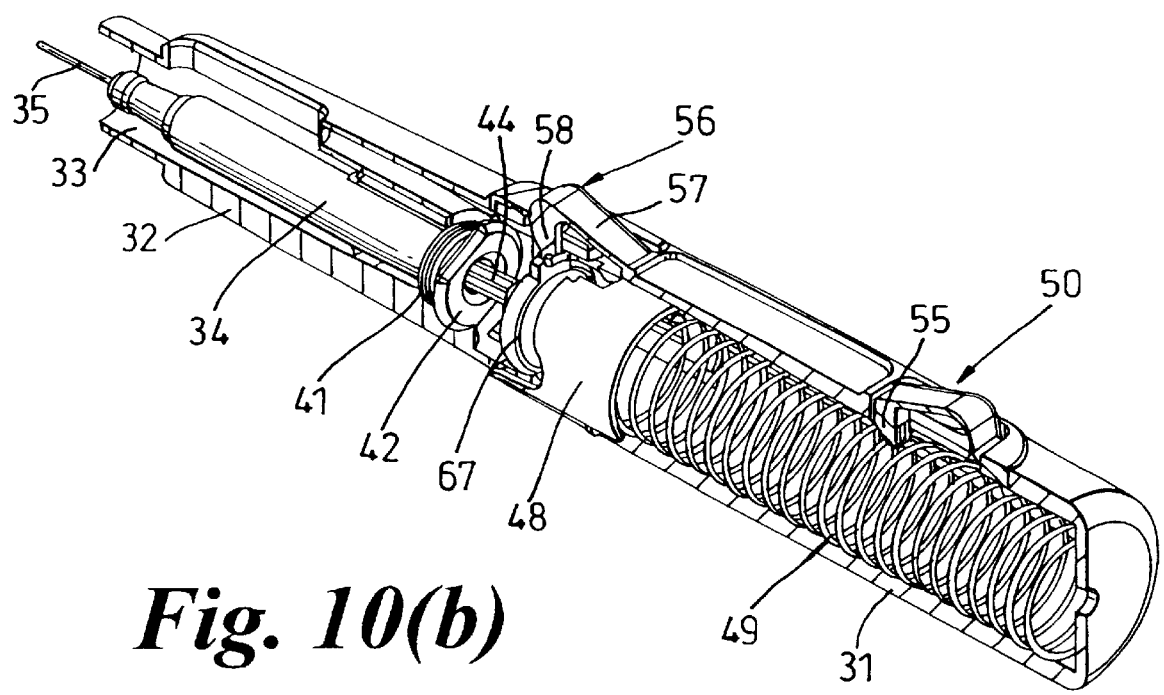
Figure 11A:
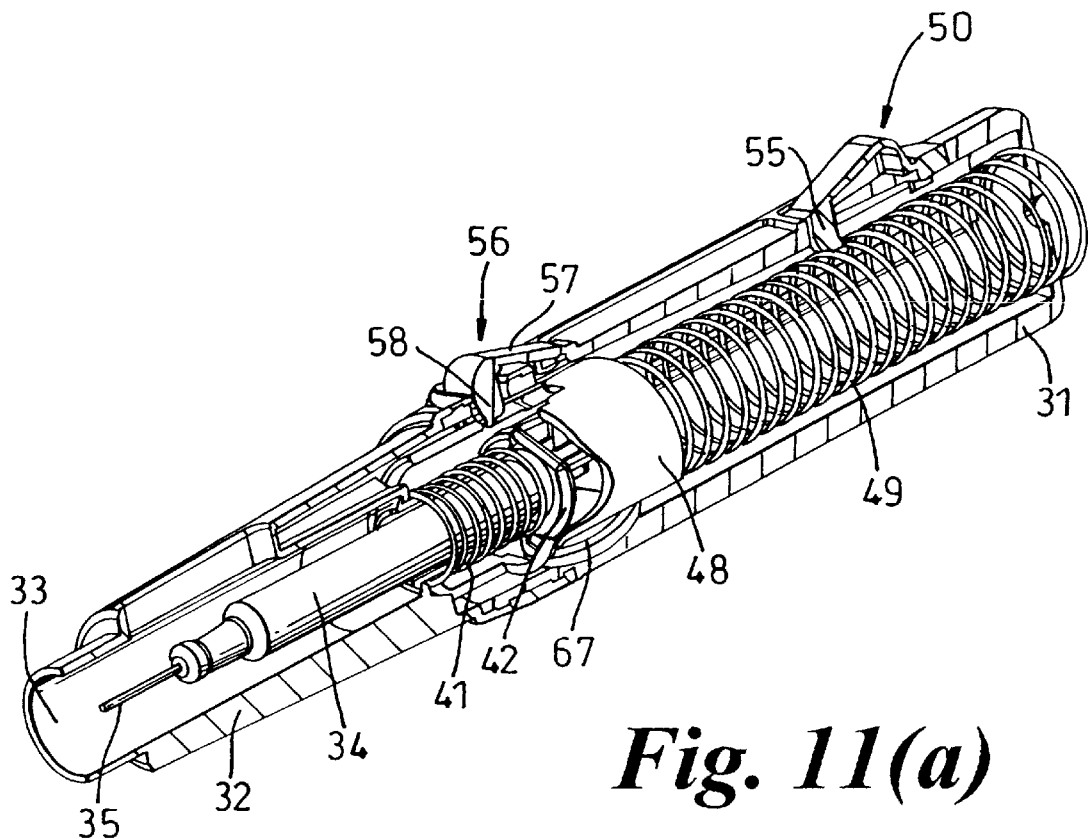
Figure 11B:
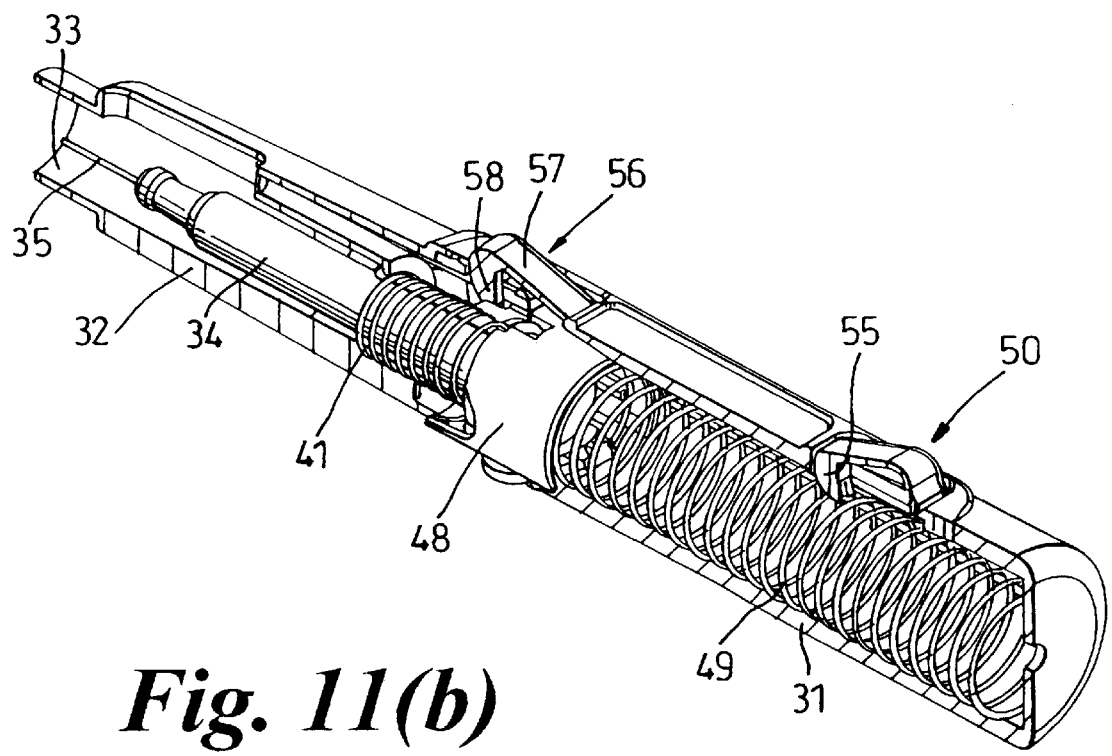
Figure 12A:
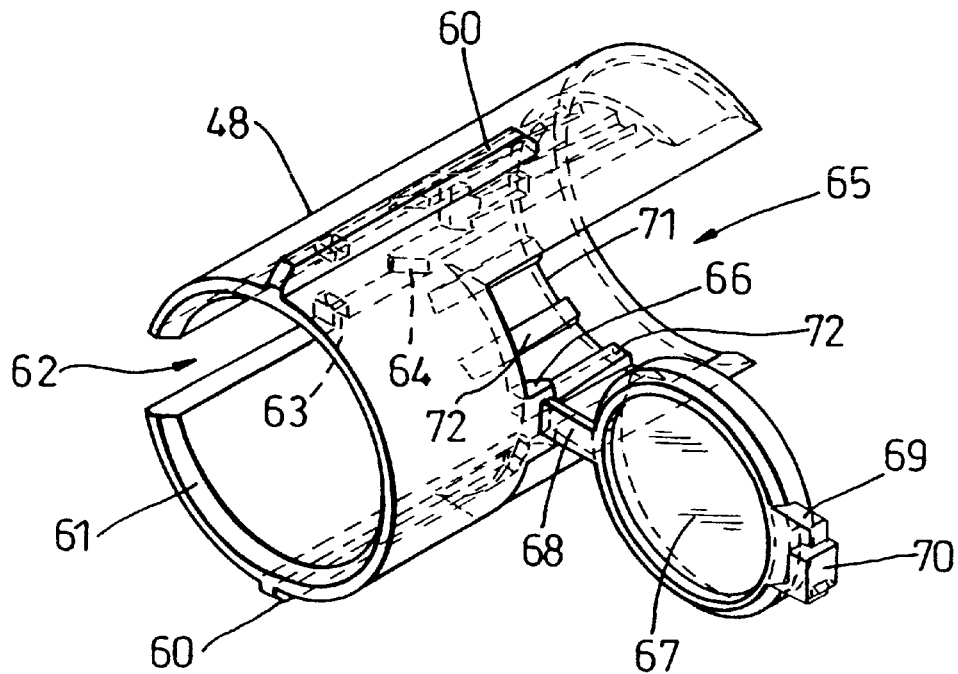
Figure 12B:
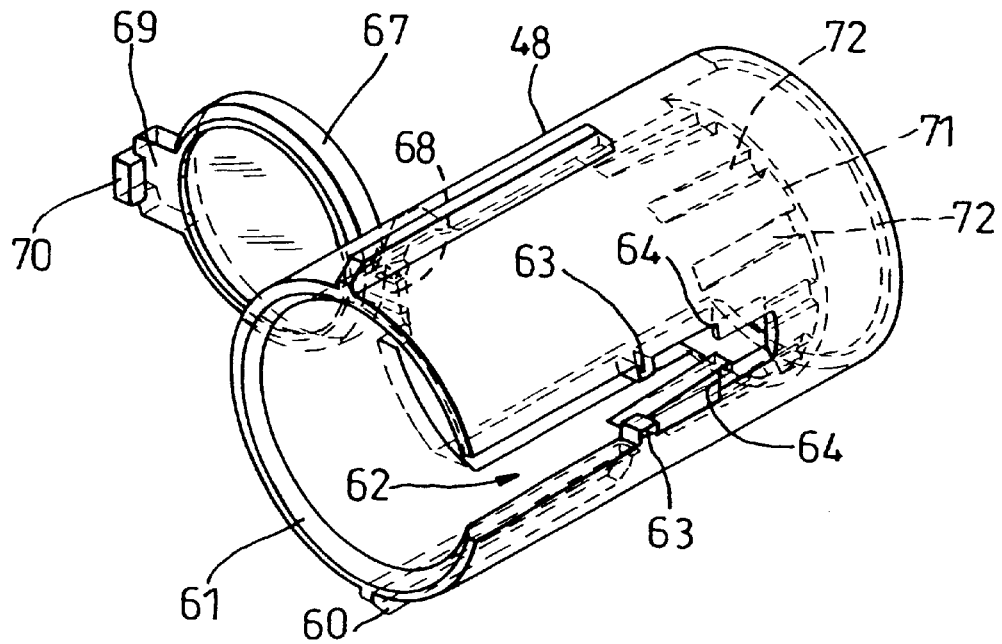

For a better understanding of the invention, one embodiment will now be described, by way of example, with reference to the accompanying drawings, in which:

FIGS. 1 to 6 are axial sections of an injection device in various stages from pre-use to post-use, FIG. 7 is an exploded perspective view of an abutment member and related parts of the drive system of the device, FIG. 8 is a detail of FIG. 1 showing a trigger mechanism, FIG. 9 shows two broken away perspective views of another injection device before use, FIG. 10 is similar to FIG. 9 but with the device as just used, FIG. 11 is similar to FIG. 9 but with the device after use, and FIG. 12 shows two perspective views of a drive member of this other device.

The device of FIGS. 1 to 8 has a generally cylindrical barrel 1 with a coned forward end 2 reducing to a mouth 3 which, in use, is pressed against the patient's skin. The barrel contains a loaded capsule 4 wish a needle 5 at its forward end initially covered by a sheath 6. A cap 7 fits to the mouth 3 and has fingers 8 projecting inside the barrel by which the sheath can be removed in known manner. The capsule is supported and guided co-axially within the barrel by two bulkheads 9 and 10 through which it passes. A return spring 11, initially extended, acts between the rear bulkhead 10 and an outward flange: 12 at the rear end of the capsule 4.

A piston 13 snugly fits into the rear of the capsule, being at the forward end of a plunger 14 whose rear end terminates at a disc 15. This lies within a shallow cup 16 as best seen in FIG. 7. In plan view its profile is that of two overlapping circles joined by parallel commotangents, and projecting radially from the tangent sides there are lugs 17. Initially, the disc 15 lies snugly up against one end of the cup 16.

The drive mechanism includes a stepped cylinder 18 with an external rearwardly facing shoulder against which a coil spring 19 acts, the other end of this spring reacting against the closed end of the barrel 1. Initially, the cylinder 18 is held in the rearward position of FIG. 1, with the spring 19 fully compressed, by a first trigger mechanism 20 shown in more detail in FIG. 8. The internal diameter of the cylinder 18 is slightly greater than the maximum span of the cup 16, and the cylinder bore is provided with two axially parallel grooves 21. At the forward end, these are widened to provide steps 22 on which the lugs 17 seat. The lugs can fit easily within the grooves 21. Externally, the larger diameter portion of the cylinder 18 has means (not shown) for preventing its rotation as it travels down the barrel, such as one or more lugs engaged in axially parallel grooves along the inside of the barrel.

The trigger mechanism 20 has a finger pad 23 integral with the barrel 1, but deformable inwardly. It bears on the end of a notched finger 24 extending forwardly and slightly outwardly from the shoulder of the cylinder 18. A lug 25 projecting in from the barrel just to the rear of the pad 23 engages in the notch and thereby holds the cylinder 18 back against the force of the spring 19. Pressure on the pad 23 bends the finger 24 inwards to free it from the lug 25.

There is a second trigger mechanism 26 at about the mid-length of the barrel 1. This also has a finger pad 27 integral with the barrel 1 and deformable inwardly. It carries an inwardly projecting finger 28 which can co-operate with the cup 16 at the end of the forward stroke.

The operation of the device is as follows, starting from FIG. 1.

Figure 2:
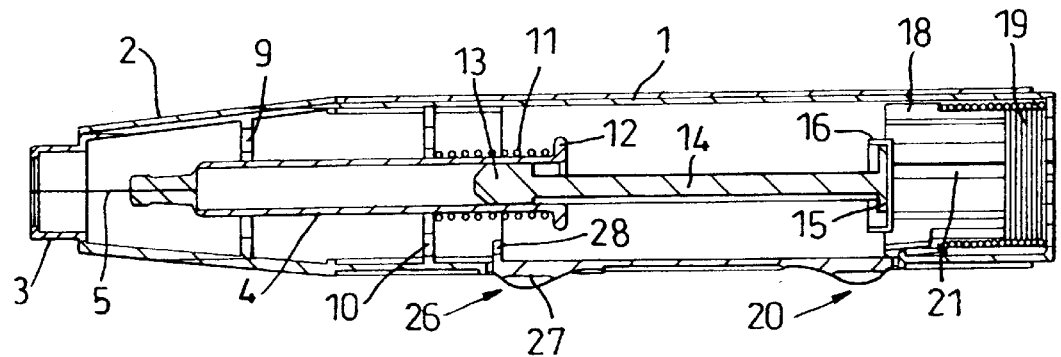
Figure 3:
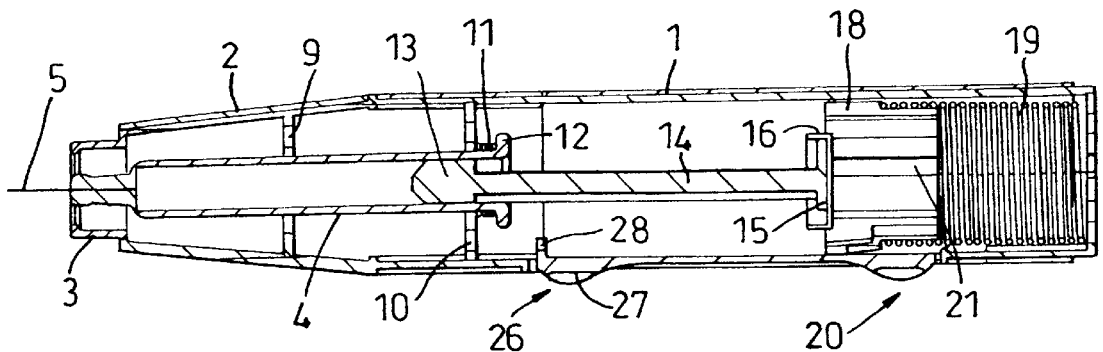
Figure 4:
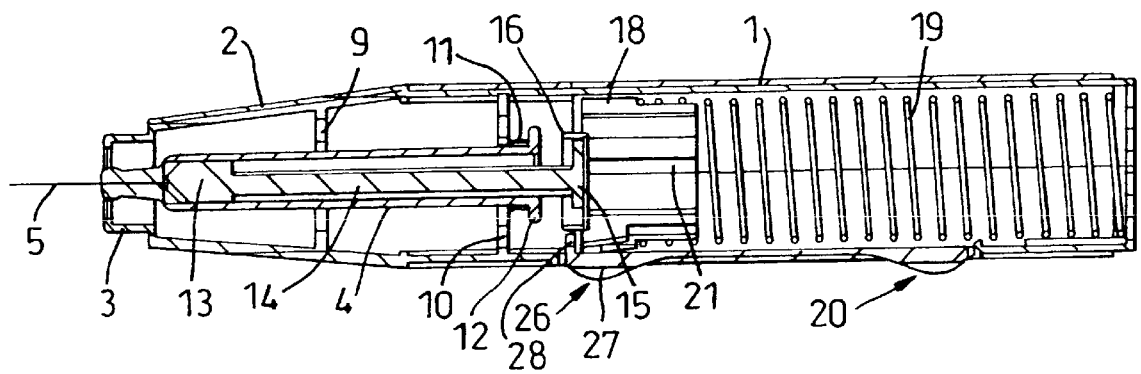
Figure 5:
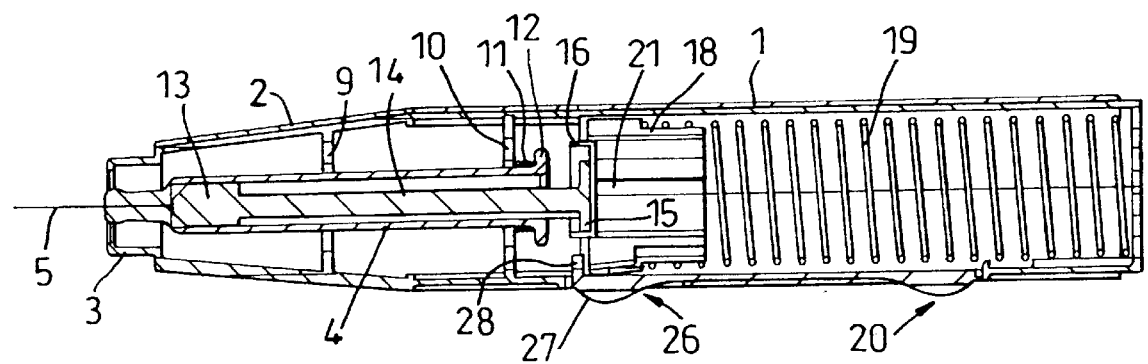
Figure 6:
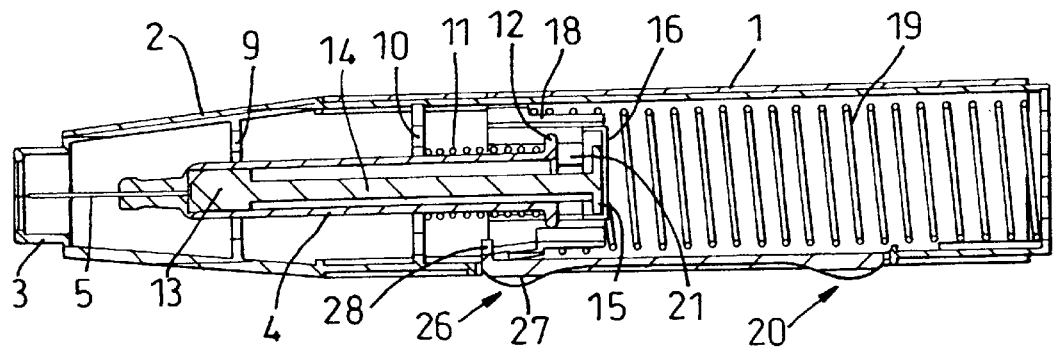

First, the cap 7 is removed, and this takes with it the sheath 6 to give the FIG. 2 condition. The mouth 3 is applied to the skin and the trigger mechanism 20 is pressed to release the drive cylinder 18. This thrusts the plunger 14 forwards, acting through the cup 16, and in particular through the lugs 17. The narrowness of the needle 5 means that the liquid in the capsule 4 has no rapid escape and so behaves as a solid. The capsule is thrust forward to the FIG. 3 position with the needle fully projecting, and it is arrested by the spring 11 becoming fully compressed.

The spring 19 continues to expand and the piston 13 is pushed forward to eject the dose. By the FIG. 4 position, this is completed, and here the cup 16 has come opposite the second trigger mechanism 26. To withdraw the needle, the pad 27 is pressed for the finger 28 to shift the cup 16 transversely of the barrel so that the disc 15 comes to rest at the opposite end from the one in which it was originally seated. At the same time, this takes the lugs 17 clear of the steps 22 and over the open ends of the grooves 21 in the cylinder 18. The return spring 11 can now act and from the FIG. 5 position the capsule 4 is thrust back to the Figure 6 position with the cup 16 travelling freely through the cylinder 18. There is nothing to hold it to the plunger, and it will fall away and remain loose within the coil spring 19. The needle is safe inside the barrel, and there is no way of firing it again. The device may therefore be safely thrown away.

The injection device of FIGS. 9 to 12 is similar in many respects to the first embodiment and equivalent parts are correspondingly referenced, with the addition of 30. Thus the barrel is indicated by 31 and the main drive spring by 49. A full, detailed description will therefore not be given.

It differs primarily in the cylinder 48 and how the disc 45 is engaged by it and released to allow needle retraction. This modified cylinder 48 is best seen in FIG. 12.

Externally, the cylinder 48 is of uniform diameter except for two diametrically opposed guide splines 60 extending rearwardly over about two thirds of the length from the internally bevelled forward end 61. Circumferentially midway between these splines 60 there is an axially parallel slot 62 open to the forward end 61 and of substantially the same length as the splines. At about its mid-length there are two opposed lugs 63 projecting towards each other from the edges of the slot 62, and towards its closed end the slot narrows at opposed shoulders 64 which slant rearwardly from the exterior.

Diametrically opposite the slot 62 there is a substantially larger cut-out portion 65, at least in circumferential extent, and this is open to the rear end of the cylinder 48 and terminates opposite the lugs 63. Central of the closed end of this cut-out 65 there is a rearward projection 66 to which a circular plate 67 is hinged by a thin web 68. The cylinder 48, plate 67 and web 68 are integrally moulded in plastics material, and the thinness of the web 68 allows it to act like a hinge. FIG. 12 shows the as-moulded condition, but the plate 67 can be swung through the cut-out 65 to be positioned as a barrier across the interior of the cylinder 48. A rectangular radial projection 69 from the plate 67 is diametrically opposite the hinge web 68, and this projection has a square button 70 at its extremity projecting rearwardly when the plate forms a barrier. It is kept in this barrier position by the projection 69 bearing against the forward sides of the lugs 63, the flexible hinge web 68 allowing the plate 67 to be manipulated to enable the projection 69 to pass forwardly of the lugs 63.

The rear end of the cylinder 48 is internally enlarged to form a locating shoulder 71 for the drive spring 49, this location being assisted by a circumferential array of shallow triangular ribs 72.

In use, the disc 45 initially bears against the barrier plate 67, the cylinder 48 being held back by the trigger 50 co-operating with the shoulders 64. The slant of those shoulders, the corresponding angle of the rear side of the lug 55 of the trigger 50, and the firmness of engagement between the lug 55 and the shoulder 64 engendered by the fully compressed drive spring 49, ensures that the retracted position is positively held.

The trigger 50, when pressed, acts in a see-saw manner to move the lug 55 radially outwards. Upon release of the cylinder 48 the action is substantially as described above, with the plunger 44 being driven forwards by the barrier plate 67.

When the injection is completed, the button 70 registers with the finger 58 of the second trigger mechanism 56. When that is actuated, the finger 58 presses on the button 70 and the hinge web 68 has sufficient length for the plate 67 to be shifted transversely in its own plane. This action pushes the projection 69 radially inside the lugs 63. But the button 70 is small enough to pass between them. It is also small enough to pass through the narrow end part of the slot 62 beyond the shoulders 64 while the outer end of the projection 69 sweeps past those shoulders. So the plate 67 is free to hinge back, and this it does through the influence of the spring 41 acting via the empty capsule 34 and plunger 44. The disc 45 brushes the plate aside and retraction is complete.

In both embodiments, the device as shown is vulnerable to premature actuation of the main trigger. To prevent this the device may be provided with a rear end cover to shield the trigger, or there might be some locking pin or tear-off tag to remove before the trigger can be actuated.

What is claimed is:

1. A one-shot injection device with a barrel-like body carrying a loaded capsule having a needle at its forward end and a spring drive system which, when released, drives the capsule forwards to project the needle from the body and eject a dose through the needle, and which thereafter can cause the capsule and needle to be retracted, wherein the spring drive system comprises a drive spring, a hollow drive member acted upon by the drive spring and initially held in a rearward position by a first trigger, an abutment member between the drive member and the rear end of the plunger whose forward end forms or acts upon a piston within the capsule, a return spring acting between the capsule and the body, and a second trigger operable when the drive member is in a forward position to move the abutment member from an engaged position in relation to the drive member to a disengaged position where the return spring can act to push the abutment member rearwardly via the capsule and its plunger, thereby retracting the needle.

2. A device as claimed in claim 1, wherein there are removable means to shield the first trigger or to prevent it being accidentally operated when the device is primed.

3. A device as claimed in claim 1 or 2, wherein the drive spring is a coil spring which when released shoots the drive member and capsule forwards, using the plunger, to project the needle and then eject the dose through the needle, the liquid contents of the capsule acting as a solid while the needle is penetrating.

4. A device as claimed in claim 3, wherein the drive member is a cylinder open at both ends and with a rearwardly facing shoulder against which the drive spring acts, the other end of the drive spring reacting against the closed rear end of the barrel.

5. A device as claimed in any preceding claim, wherein the return spring is a coil spring surrounding the capsule and offering little resistance to the drive spring.

6. A device as claimed in any preceding claim, wherein the abutment member is free of the drive member and in its engaged position is peripherally held against a forward facing shoulder formation of the drive member, and wherein the second trigger actuation shifts the abutment member to the disengaged position, clear of the shoulder, where it is free to be pushed rearwardly through the drive member.

7. A device as claimed in claim 6, wherein the shift from the engaged to the disengaged position is laterally of the barrel.

8. A device as claimed in claim 6, wherein the shift from the engaged to the disengaged position is rotational about the axis of the barrel.

9. A device as claimed in any one of claims 1 to 5, wherein the abutment member is hinged to the drive member and in its engaged position is held across a passage through the drive member by a formation diametrically opposite the hinge co-operating with a detent on the barrel, and wherein the shift from the engaged to the disengaged position is by the second trigger releasing said formation from the detent, thereby allowing the abutment member to hinge back and clear the passage for the plunger.

10. A device as claimed in claim 9, wherein the drive member and abutment member are integrally moulded of plastics material, with a thin web forming the hinge and allowing diametral shift of the abutment member for release of said formation from the detent.

* * * * *